United States Patent [19]
Weston

[11] Patent Number: 5,391,174
[45] Date of Patent: Feb. 21, 1995

[54] ENDOSCOPIC NEEDLE HOLDERS

[76] Inventor: Peter V. Weston, 705 Oak Hills Medical Bldg., 7711 Louis-Pasteur Dr., San Antonio, Tex. 78229

[21] Appl. No.: 800,230

[22] Filed: Nov. 29, 1991

[51] Int. Cl.$^6$ .............................................. A61B 17/00
[52] U.S. Cl. .................................... 606/148; 606/205; 606/207
[58] Field of Search ............... 606/147, 144, 139, 148, 606/187, 185, 205, 206, 207, 208, 209, 1

[56] References Cited

U.S. PATENT DOCUMENTS

| | | | |
|---|---|---|---|
| 2,905,178 | 9/1959 | Hilzinger, III | 606/1 |
| 4,493,323 | 1/1985 | Albright et al. | 606/144 |
| 4,562,839 | 1/1986 | Blake, III et al. | 606/143 |

Primary Examiner—Stephen C. Pellegrino
Assistant Examiner—Jeffrey A. Schmidt
Attorney, Agent, or Firm—David G. Henry

[57] ABSTRACT

The invention is embodied in suture needle holders particularly useful in endoscopic surgical procedures. The instruments either incorporate a fixed suture needle or facilitate the secure, reversible grasping of a suture needle. Actuation of the instrument steadily directs the needle through the path of an arc thereby facilitating passage of the needle through tissue for suture placement. Actuation of the instruments involves simple opposed finger movement which obviates the often times difficult rotational wrist movement necessary for use of needle holders in the prior art.

5 Claims, 8 Drawing Sheets

ENDOSCOPIC NEEDLE HOLDERS

BACKGROUND OF THE INVENTION

1. Field of The Invention

Applicant's invention relates to surgical instruments and more particularly to methods and techniques of suturing within a body cavity such as the abdominal cavity of a human or an animal.

2. Background Information

Many surgical operations are being performed endoscopically and as technology advances new applications are being developed. The primary advantage to the patient of laparoscopic surgery is that the post operative recovery period is dramatically shortened thereby reducing the period of hospitalization. In addition, patients return to work much sooner than after surgery with large incisions.

Some of the technical problems encountered by those practicing laparoscopic surgery includes the need to perform delicate three dimensional procedures while looking at a two dimensional video screen since laparoscopy is performed with the operator looking solely at a two-dimensional video screen for guidance. This makes it difficult to grasp and manipulate suture needles because of the complete loss of depth perception.

Applying the existing art requires that, once a suture needle has been grasped using presently available instruments, the needle is inserted into the tissues by way of rotation of the instrument which, in turn, is effected only through a rotational movement of the user's wrist. This is often difficult and complicated because the operator typically has only a very limited range of movement caused by the constraining effect of the substantially immobile abdominal wall coupled with the location and position of the laparoscopic cannula through which the needle holding instrument must pass. These problems, coupled with the difficulties associated with the present generation of suture needle holders, make suture placement time consuming. This, in turn, translates into more expensive and at least slightly more risky procedures.

Most current endoscopic needle holders are modifications of conventional needle holders where the needle is simply grasped by hinged jaws. A characteristic necessarily common to most endoscopic instruments—being both long and slender—works counter to providing an effective needle handling capacity when applying the techniques of the prior art. The hinged jaws which are common to existing needle grasping mechanisms are necessarily small. To the extent that mere scissor-like mechanisms are used to apply the compressive force to the hinged jaws, the length of the instrument combined with its low mass prevents generating aim effective compressive force on the grasped portion of the needle. This results in a tendency of the needle to rotate in the jaws as the surgeon attempts to place a suture.

A further difficulty with current needle holders is that once the needle is secured in the needle holder it is often difficult to advance the needle through the tissues in the desired direction because of the limitations caused by the location of the endoscopic cannula and the technical difficulty in rotation of the operator's wrist. Occasionally, the surgeon has to pass the needle more than once in order to obtain the correct placement of the needle.

The present invention provides an instrument which allows a suture needle to be rotated between desired positions, in the process passing through a definite and specific arc lying in a stationary plane. The needle's movement is effected, not through rotation of the instrument through rotation of the user's wrist, but rather by simple opposition of the thumb and the second and third fingers as applied to the actuating members of Applicant's new instrument. Accordingly, Applicant's invention allows for accurate and less difficult placement of sutures, and the problems and difficulties associated with wrist rotation as required when practicing the prior art are thereby wholly eliminated.

Applicant's instruments also effect a secure grasp on a suture needle notwithstanding the instrument's size and shape being ideal for endoscopic surgery.

Prior issued patents which are known to Applicant and which relate to needle holders which are used during surgical operations are revealed in the discussion to follow.

The problem of adequately securing a needle has been partially addressed through an instrument manufactured by COOK OBGYN and disclosed in U.S. Pat. No. 5,015,250. The COOK OBGYN instrument involves a needle lying in a groove in a hollow channel. The needle is secured by a spring loaded rod which immobilizes the needle in the channel. Nevertheless, the disadvantages of this instrument are that (1) the spring is very strong and requires great force to grasp and release the needle, and (2) the handle portion is not rotatable relative to the remainder of the instrument such that placement of the needle in the tissues requires a rotational movement of the wrist and arm. This makes precise placement of the needle very difficult.

U.S. Pat. No. 4,898,157 issued to Messroghli et al is a needle holder not specifically designed for endoscopic use. Pressure on the handles is converted into a longitudinally directed force which is converted into pressure on a movable jaw to grasp a surgical needle. Once again, it is believed that even if modified, the force applied to the needle would be inadequate to truly secure the needle under many endoscopic surgery conditions.

A needle taught by Yasukata Eguchi et al (U.S. Pat. No. 4,527,564) has a rectangular proximal end which allows for rigid grasping by a needle holder. The needle is not, however, suitable for endoscopic surgery.

U.S. Pat. No. 4,760,848 issued to Hasson addresses the difficulties associated with wrist movement in endoscopic surgery. Hasson's invention uses conventional needle holding jaws that self lock. Rotation of the needle during its insertion is effected by rotation of the instrument with the thumb and fingers. The grasping mechanism is suitable for very small needles used in microsurgery, but does not grasp the needle sufficiently securely for laparoscopic surgery.

U.S. Pat. No. 4,621,640 issued to Mulhollan discloses a mechanical needle carrier which holds a surgical needle for use during endoscopic surgery. This is a small needle which is contained within the sheath of the instrument and is advanced through tissues by rotation of a knurled rod. The size of the needle is limited by the diameter of the shaft and is too small to be applicable to abdominal or thoracic endoscopic surgery. A similar problem plagues the suturing instrument described in U.S. Pat. No. 4,557,265.

U.S. Pat. No. 4,923,461 issued to Caspari discloses a method of suturing for arthroscopic surgery that incorporates a hollow needle and a mechanism whereby suture may be fed through the hollow needle.

U.S. Pat. Nos. 4,484,580, 4,417,532 and 4,406,237 issued respectively to Nomoto et al, Eguchi Yasukata, and Yasukata Eguchi et al, as well as earlier referenced U.S. Pat. No. 4,527,564, all teach needles each having a distal eye through which suture thread passes. These needles are each rigidly attached to a shaft which allows precise placement, but are locked in a fixed position and cannot be retracted to allow passage through an endoscope. Also, these needles are necessarily of a size which preclude their exit through an endoscope, even if not locked in place. Even if these needles were to be reduced in size sufficiently to pass through an endoscope, they would be too small for most abdominal or thoracic applications.

U.S. Pat. No. 4,935,027 issued to Yoon teaches a suturing instrument which places suture material through tissues endoscopically by grasping tissues between two hollow jaws and passing suture from one to the other.

U.S. Pat. No. 4,164,225 issued to Johnson et al also grasps tissue between two jaws. Activation of a plunger allows a suture bearing needle to pass from one jaw to the other and thereby pass suture material through the tissues. A similar achievement is performed by U.S. Pat. No. 3,946,740 issued to Bassett.

U.S. Pat. No. 4,793,379 issued to Weinrib describes a microsurgical needle holder which has a hook on one jaw to assist in grasping the needle securely.

U.S. Pat. No. 3,842,840 issued to Schweizer discloses a suture clamp in which a needle is driven from one jaw to the other carrying a length of suture through the grasped tissues. Because of the scissor-like action of the Jaws this instrument is not suitable for endoscopic surgery.

Mulhollan in U.S. Pat. No. 4,597,390 describes a novel endoscopic needle holder in which the needle is firmly held by slots in two hollow members. The needle is inserted into tissues by rotation of the shaft of the instrument.

U.S. Pat. No. 3,871,379 issued to Clarke describes several endoscopic instruments, one of which is an articulated needle with a distal eye. This instrument allows a curved needle to be inserted through an endoscopic cannula. Abduction of the handles causes the needle to be displaced laterally, but does not cause it to travel through a specific arc.

SUMMARY OF THE INVENTION

It is an object of the present invention to provide a novel and nonobvious surgical needle holder which is useful in endoscopic procedures.

It is another object of the present invention to provide a novel and nonobvious surgical needle holder which, more effectively than apparatuses in the prior art, secures a needle for facilitating the effective use thereof in endoscopic procedures.

It is another object of the present invention to provide a novel and nonobvious surgical needle holder which directs a needle through a desirable path through tissue, without requiring rotation of the wrist by a user.

It is another object of the present invention to provide a novel and nonobvious surgical needle holder which facilitates accurate suture placement in endoscopic surgical procedures.

It is yet another object of the present invention to provide a novel and nonobvious surgical needle holder which, notwithstanding its facility for securely holding a needle for use, permits easy disengagement of the needle for withdrawal through an endoscope.

In satisfaction of these and related objectives, Applicant's present invention provides a first device for securely grasping a surgical needle, in turn, for quickly, precisely and resolutely directing the needle through tissue for effective suture placement. The device also substantially reduces the force and hand manipulation required to place the suture when compared with currently available needle holders. Still further, the first device allows easy disengagement of the needle for withdrawal through an endoscope.

Actuation of each of Applicant's devices very simply involves depressing a plunger-like member which moves relative to the balance of the device predominantly a tube-like member). A user's thumb actuates the plunger while the second and third fingers, positioned in appropriate retaining members, oppose the force applied by the thumb to maintain the device's desired position relative to the patient and to properly orient the actuating force. This is in marked contrast to the difficult manipulations required for effective use of the effective instruments presently available. The jaws of this first needle holder are different from standard needle holders in that the first jaw has an oblique channel through which the needle passes. The needle is securely lodged in the first jaw's channel by action of the second jaw which superposes the needle. The first and second jaws respectively exhibit halves of a complimentary ridge/recess structure for securing their relative positions and, in turn, the needle in its proper position.

A second feature of this first device is that the jaws are not attached to a fulcrum which allows them to be held together by pressure on the side opposite the fulcrum. They are held together by external pressure exerted by the walls of a channel defined in the device through which the jaws are advanced during use. The channel defines a crescent path which directs a needle through 90 radian of curvature during actuation of the device. When the jaws of the needle holder are completely advanced beyond the channel, they protrude from the distal end of the instrument, external pressure no longer is present and a spring forces the jaws apart. The needle can then be easily disengaged from the device.

Another embodiment of Applicant's invention is an instrument with a rigidly attached needle which exhibits an eye near the needle's point (much like the needle of the Yasukata instrument). The needle of this instrument of Applicant's invention is not intended to be released from the instrument during use, but does direct the needle in substantially the same manner as does the earlier described instrument.

Yet another embodiment of Applicant's invention prescribes a fixed needle, actuated and acting as the needles of the above-described embodiments. However, the needle of this embodiment exhibits an eye which can be opened by remote manipulation for most easily releasing the suture thread.

The advantages of the instruments of Applicant's invention are that they will facilitate suture placement and shorten the time of surgery and thereby reduce the risks of surgery.

DETAILED DESCRIPTION OF THE PREFERRED EMBODIMENT

Figure 1:
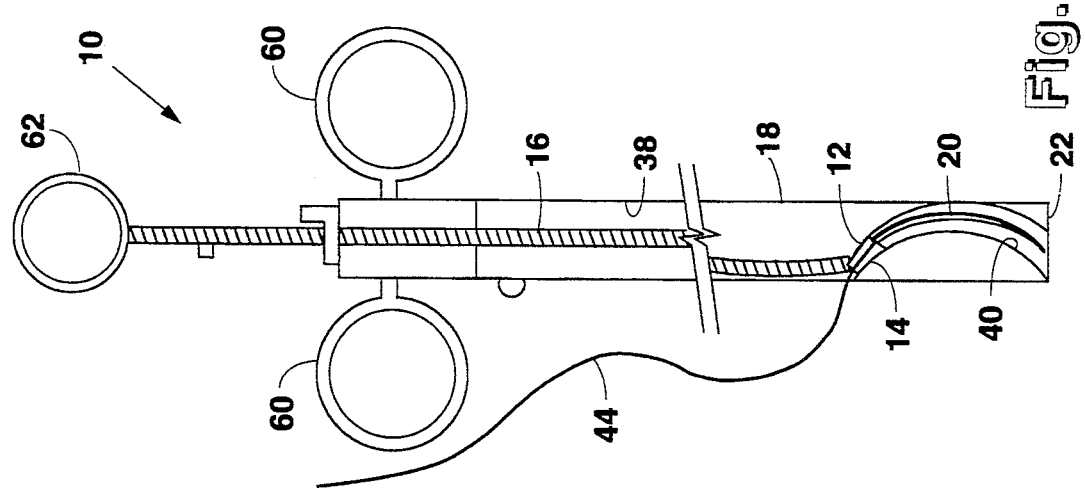
FIG. 1 is an elevational, cross sectional view of a needle holder of Applicant's invention with the needle fully retracted prior to use.

Referring to FIG. 1, a suturing instrument of Applicant's invention is identified in its entirety by the reference numeral 10. The principle components of the instrument 10 are the grasping members 12 and 14, the push rod 16 to which the first grasping member 12 is attached, and the channel member 18 from and through which the push rod 16 extends.

Figure 3:
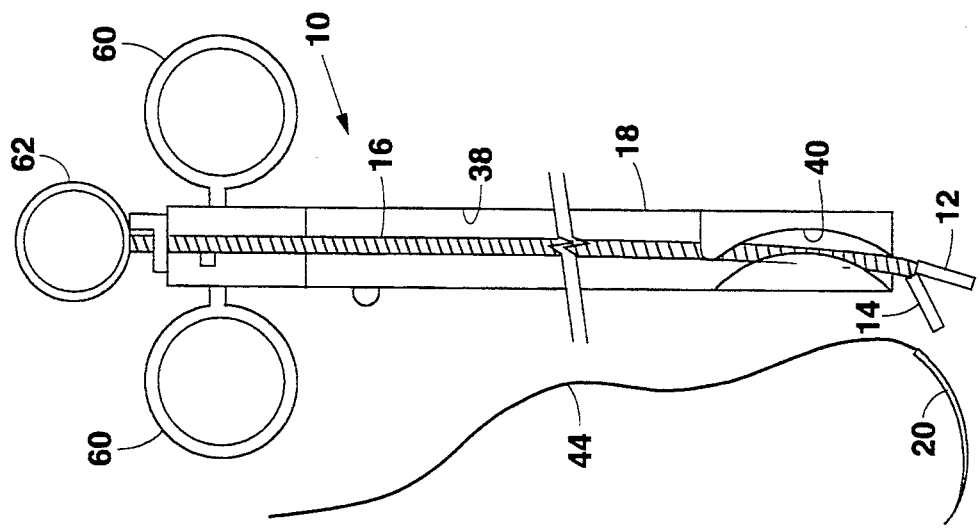
FIG. 3 is an elevational, cross sectional view of a needle holder of Applicant's invention with the needle fully extended such as after use when the needle is to be disengaged and removed from the instrument.
Figure 2:
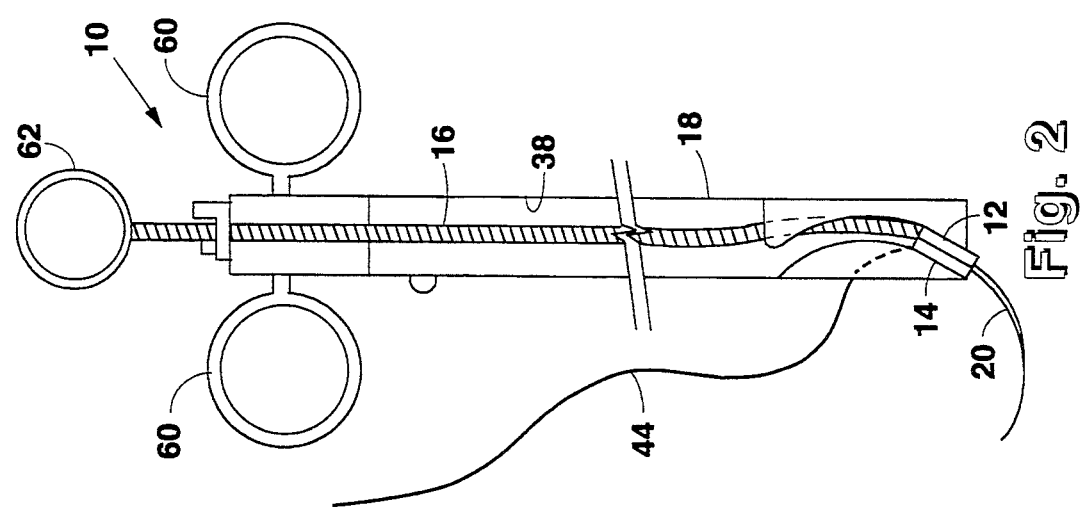
FIG. 2 is an elevational, cross sectional view of a needle holder of Applicant's invention with the needle partially extended such as during use.

Referring jointly to FIGS. 1, 2 and 3, instrument 10 is for directing the tip of a surgical needle 20 through a crescent path beginning at the distal end 22 of the channel member 18 and ending at a point where the needle has passed through approximately 90 radian of curvature.

Referring jointly to FIGS. 1, 2, 3, and 4, the grasping members 12 and 14 are for securely holding the surgical needle 20 as it is urged through a patient's tissue under force applied by way of the push rod 16. As depicted in FIG. 3, once the push rod 16 is fully depressed with the needle 20 having passed fully through its prescribed path, the grasping members 12 and 14 are allowed to separate and to thereby disengage the needle 20.

Figure 4:
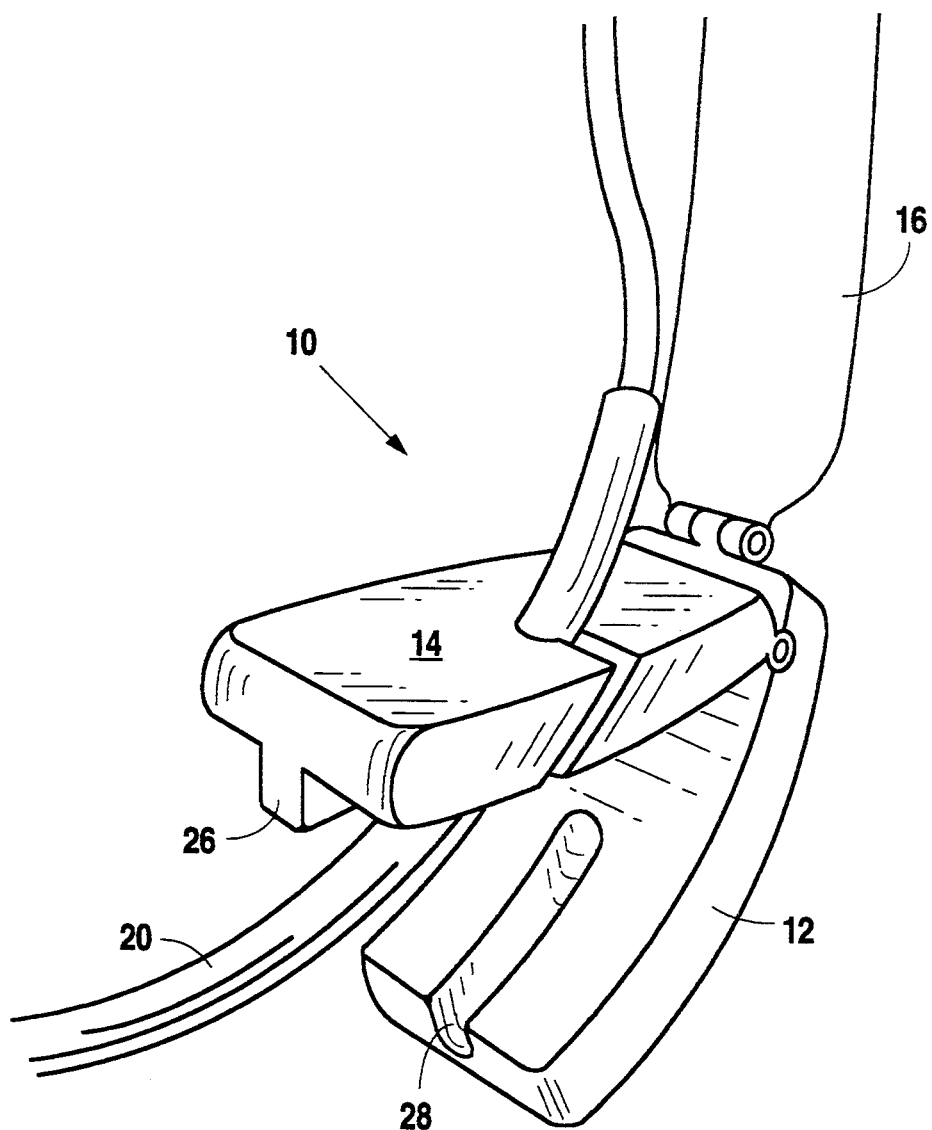
FIG. 4 is a perspective view of the jaw members and of their relative arrangement vis a vis the push rod and a suture needle.
Figure 5:
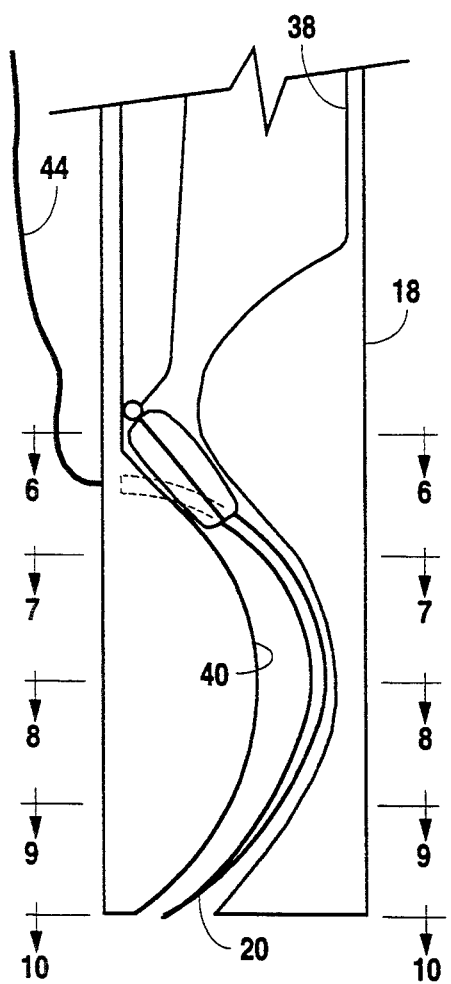
FIG. 5 is a sagittal cross sectional view of the lower portion of the shaft of the instrument showing the needle residing in the crescent channel such as prior to use.
Figure 6:
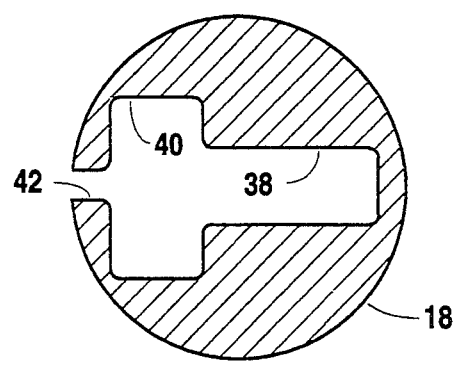
FIG. 6 is a cross sectional view of the lower portion of the channel member along line 6—6.
Figure 7:
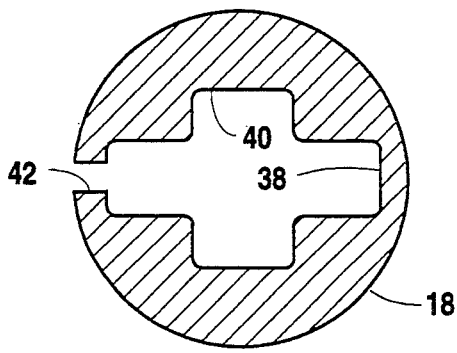
FIG. 7 is a cross sectional view of the lower portion of the channel member at second position along line 7—7.
Figure 8:
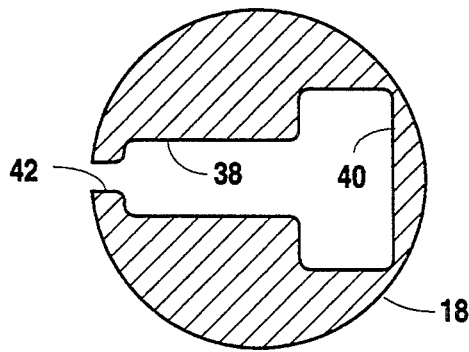
FIG. 8 is a cross sectional view of the lower portion of the channel member at a third position along line 8—8.
Figure 10:
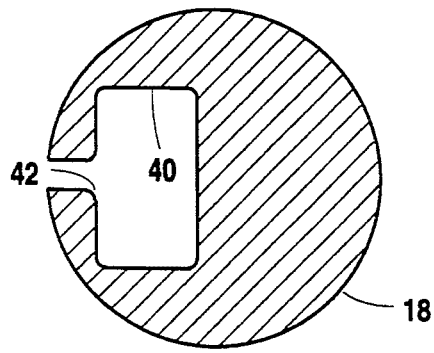
FIG. 10 is a cross sectional view of the lower portion of the channel member at a fifth position along line 10—10.
Figure 9:
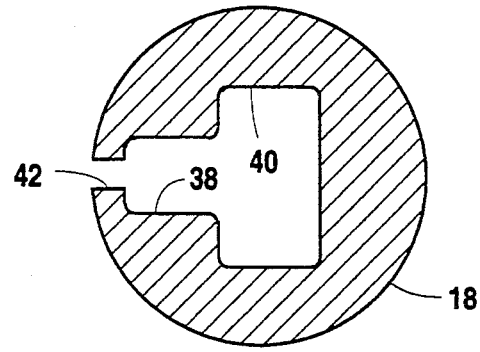
FIG. 9 is a cross sectional view of the lower portion of the channel member at a fifth position along line 9—9.

FIG. 4 depicts in detail the configurations and contours of grasping members 12 and 14. The grasping member 14 exhibits an aperture 24 through which a needle 20 extends during use of the instrument 10. Grasping member 14 also exhibits a ridge 26 for which is provided a complimentary recess 28 in grasping member 12. The intercourse between the ridge 26 and the recess 28 when the grasping members 12 and 14 are most closely approximated during use of the instrument 10 is for insuring the proper relative orientation of the grasping members 12 and 14 for securely holding a portion of needle 20 between the grasping members 12 and 14.

Grasping member 12 is hingedly attached to the distal end 32 of the push rod 16 by way of hinge 34. This hinged relationship permits the pair of grasping members 12 and 14 to change orientations relative to the push rod 16 as the push rod 16 is depressed. This is necessary because, while the grasping members 12 and 14 travel a crescent path during use of instrument 10, the push rod 16 travels substantially in a linear path within the channel member 18. Grasping member 14 is hingedly attached to grasping member 12 by hinge 36.

Referring principally to FIGS. 1, 2, 3, 5, 6, 7, 8, 9 and 10, the internal space of the channel member 18 defines a rod channel 38 through and from which extends push rod 16. Near the distal end 22 of the channel member 18, the interior contour of the channel member 18 is such that it defines a crescent channel 40 and a more constrained segment of the rod channel 38. The rod channel 38 and the crescent channel 40 are in communication as is clear from FIGS. 6, 7, 8, 9 and 10. The crescent channel 40 is also in communication with space exterior to the channel member 18 by way of an elongate slot 42 for accommodating a suture thread 44 which is attached to the needle 20.

The crescent channel 40 is defined within the channel member 18 such that it governs and changes the orientation of the grasping members 12 and 14 as they move under force applied by way of the push rod 16. The result is that needle 20 follows a crescent path of approximately 90 radian as the push rod 16 is fully depressed. This path is ideal for directing the needle 20 through a patient's tissue for properly setting a suture thread 44.

The size and shape of the crescent channel 40 along its entire length is such that the grasping members 12 and 14 are maintained in a tightly closed relationship so long as they are within the bounds of the crescent channel 40. When, by fully depressing the push rod 16, the grasping members 12 and 14 extend beyond the distal end 22 of the channel member 18, they are allowed to separate and to release the needle 20.

Figure 11:
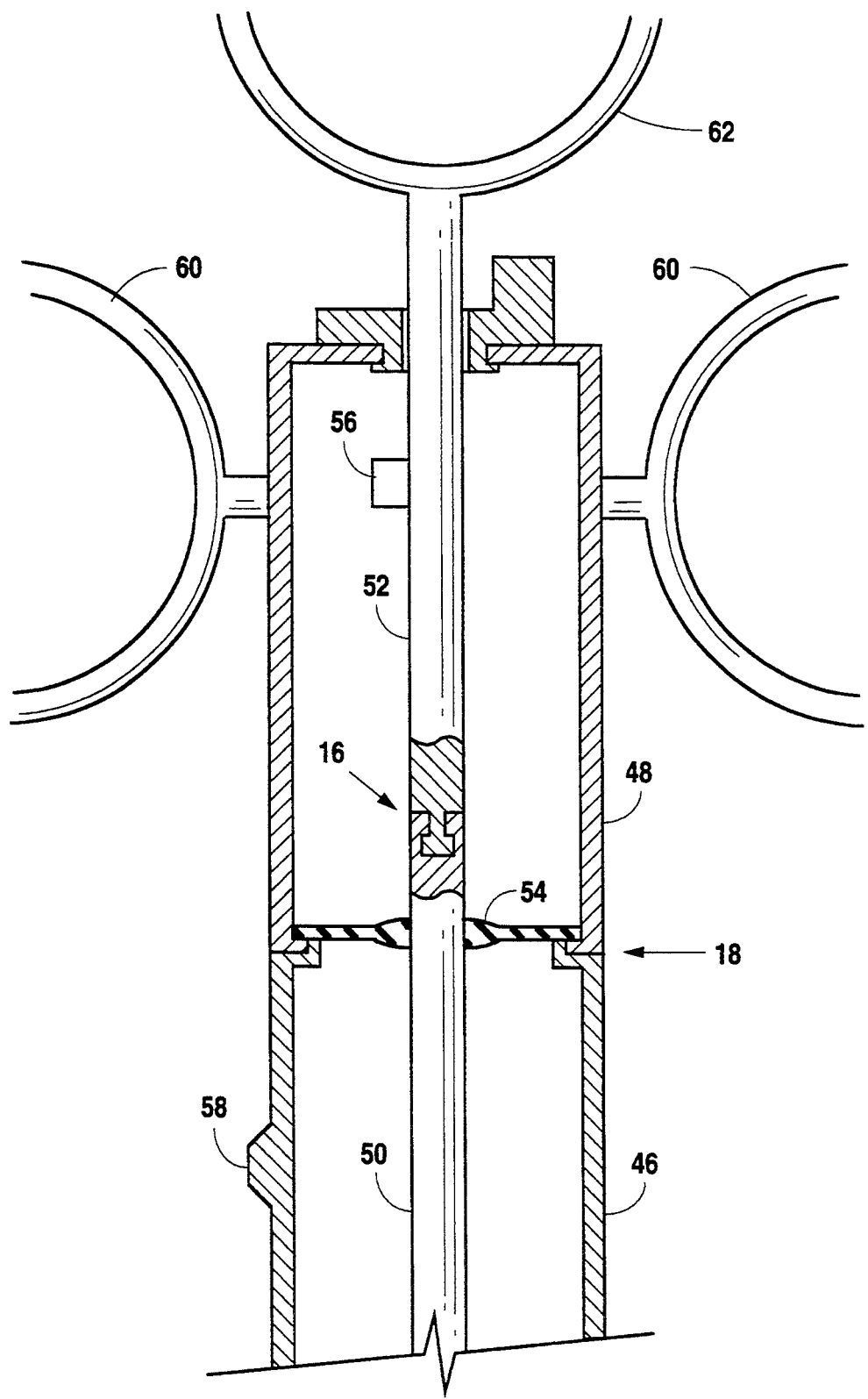
FIG. 11 is a sagittal cross sectional view of the upper portion of the shaft of the instrument showing in detail the component sections of the channel member and of the push rod, as well as other details not visible in other views.

Referring principally to FIG. 11, the channel member 18 is comprised of two sections 46 and 48. Sections 46 and 48 are joined such that either can axially rotate independent of the other. The push rod 16 is also comprised of independently, axially rotatable segments 50 and 52. This arrangement permits proper orientation of the needle 20 (as dictated by section 46 of the channel member 18 and section 50 of the push rod 16) independent of section 48 of the channel member 18 and segment 52 of the push rod 16. In this manner, a user of instrument 10 can position his or her actuating hand in whatever orientation is most comfortable anchor effective for actuating the instrument 10.

At the margin between sections 46 and 48 of the channel member 18 is a gas seal 54. The gas seal, which is conventional in design, is necessary to prevent unintended evacuation by way of the instrument 10 of gasses which, in many abdominal procedures, are maintained under pressure in the abdominal cavity of a patient.

Affixed to segment 52 of the push rod 16 is a stop 56 which is positioned for arresting further advancement of the push rod 16 through the channel member 18 to prevent the grasping members 12 and 14 extending out of the crescent channel 40 beyond the distal end 22 of the channel member 18.

Figure 12:
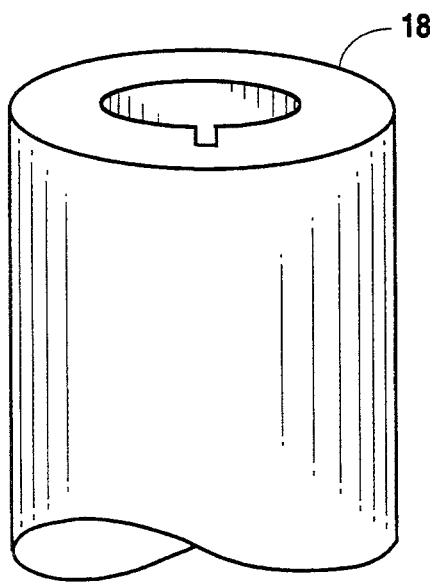
FIG. 12 is an exploded perspective view of the stop release portion of an instrument of Applicant's invention.

Referring in combination to FIGS. 11 and 12, if the operator wishes to release the needle 20 from the grasping members 12 and 14, the operator will rotate the stop release 64 so as to clear the way for the stop 56 to pass into the rod channel 38 to, in turn, permit grasping members 12 and 14 to exit the crescent channel 40 for releasing the needle 20 therefrom.

Figure 13:
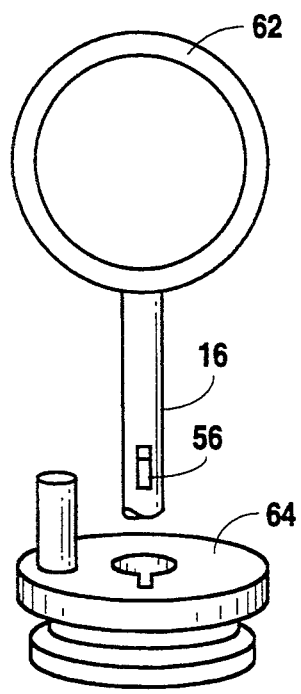
FIG. 13 is a top plan view of an alternative embodiment for a stop release for the instruments of Applicant's invention with the stop release being depicted in the closed position.
Figure 13:
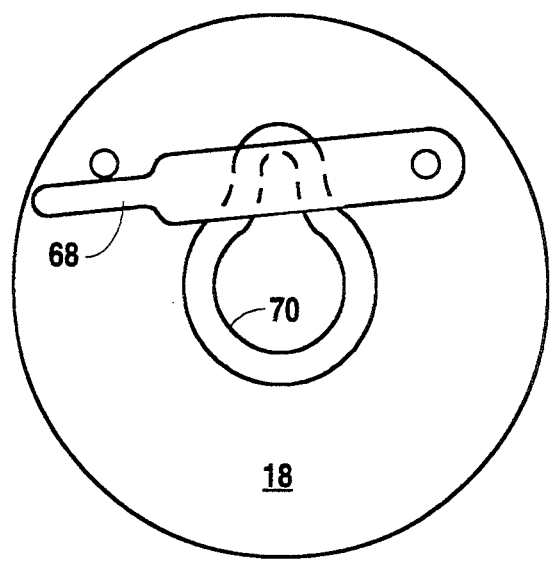
Figure 14:
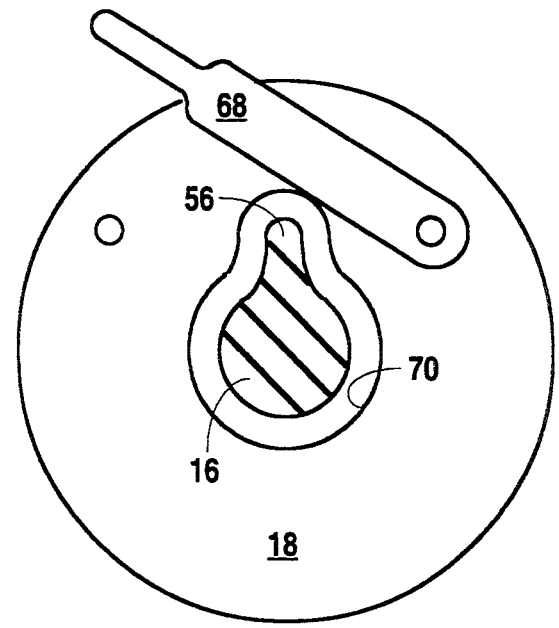
FIG. 14 is a top plan view (with a partial cross section of the push rod included) of an alternative embodiment for a stop release for the instruments of Applicant's invention with the stop release being depicted in the open position.

Referring to FIGS. 13 and 14, an alternative embodiment for a stop release 68 is shown. In this embodiment, the rod orifice 70 through which push rod 16 passes, is shaped so as to also accept passage of stop 56 therethrough when stop release 68 is in the open position. Some practitioners may, because of the partial loss of tactility caused by surgical gloves, prefer this simple lever-like stop release 68 rather than the rotatable stop release 64 depicted in FIG. 12.

Referring again principally to FIG. 11, affixed to section 46 of the channel member ? .8 is a direction indicator 58, the orientation of which indicates the orientation of the needle 20 which is deep inside a patient.

Affixed to opposing sides of the section 48 of channel member 18 are two finger rings 60. Affixed to the proximal end of segment 52 of the push rod 16 is a thumb ring 62. Grasping the instrument 10 using finger rings 60 and thumb ring 62 for use of instrument 10 is not unlike grasping the well-known, similarly configured hypodermic syringe (not shown in the figures).

The preferred embodiment of instrument 10 consists of a long shaft approximately 40 centimeters in length and the external diameter is approximately 10 millimeters.

Figure 15:
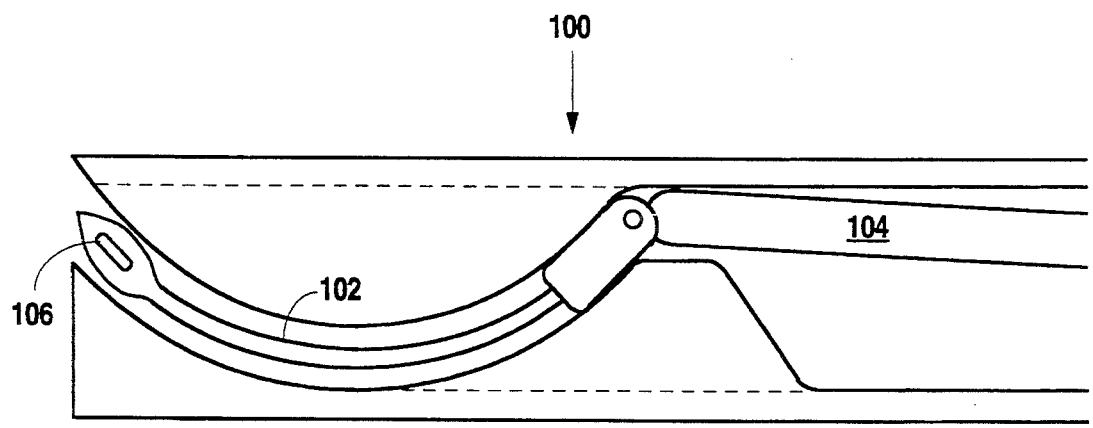
FIG. 15 is an elevational, cross sectional view of the lower portion of an alternate embodiment of Applicant's invention which involves a fixed needle with a distally positioned needle eye, the needle being shown in the fully retracted position.
Figure 16:
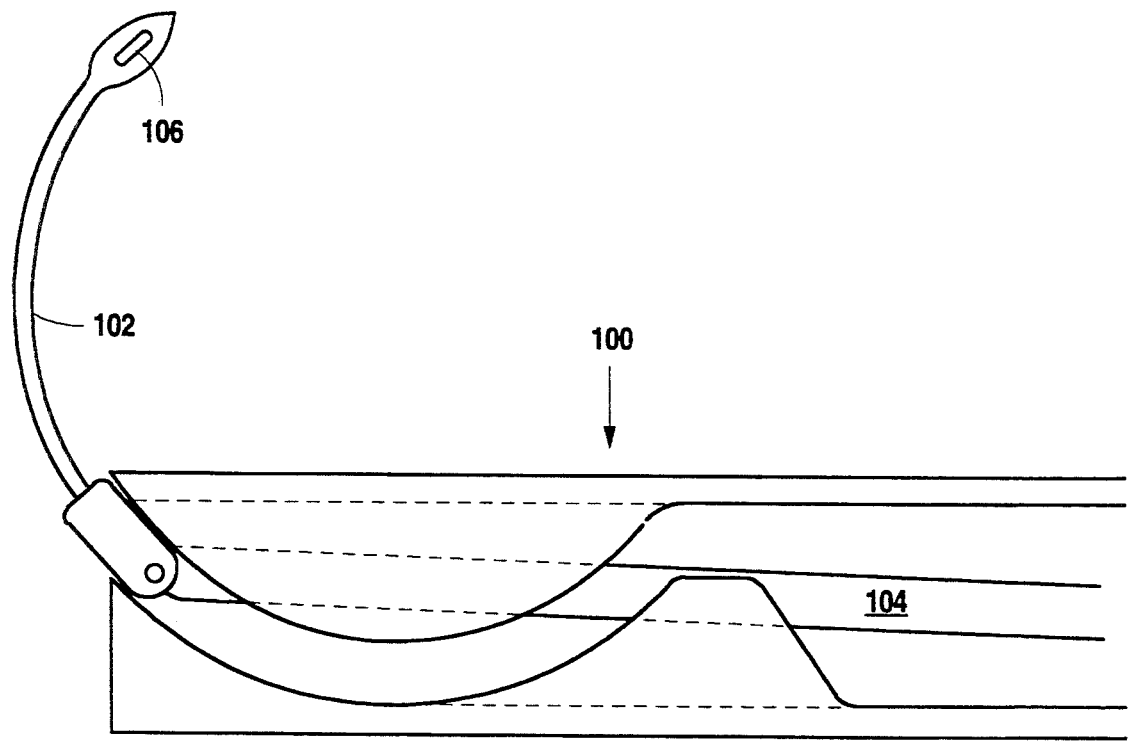
FIG. 16 is an elevational, cross sectional view of the lower portion of an alternate embodiment of Applicant's invention which involves a fixed needle with a distally positioned needle eye, the needle being in a fully extended position.

Referring principally to FIGS. 15 and 16, an alternative embodiment of Applicant's invention (instrument 100), instead of using a conventional suture needle, employs a suture needle 102 which exhibits an eye 106 near its tip as opposed to the other end. Suture needle 102 is permanently attached to rod 104 (hinge 108.) Otherwise, instrument 100 employs the same principles for the advancement of the suture needle 102 and provides substantially the same benefits as instrument 10.

Use of instrument 100 will involve passing a length of suture thread (not shown) through the eye 106 of the suture needle 102 by the scrub technician prior to handing it to the surgeon. Once in the body cavity the suture needle 102 is advanced and the suture needle 102, together with the thread is passed through the tissues which is to be sutured. With another instrument (not shown) the thread is grasped and the suture needle 102 is withdrawn.

Figure 17:
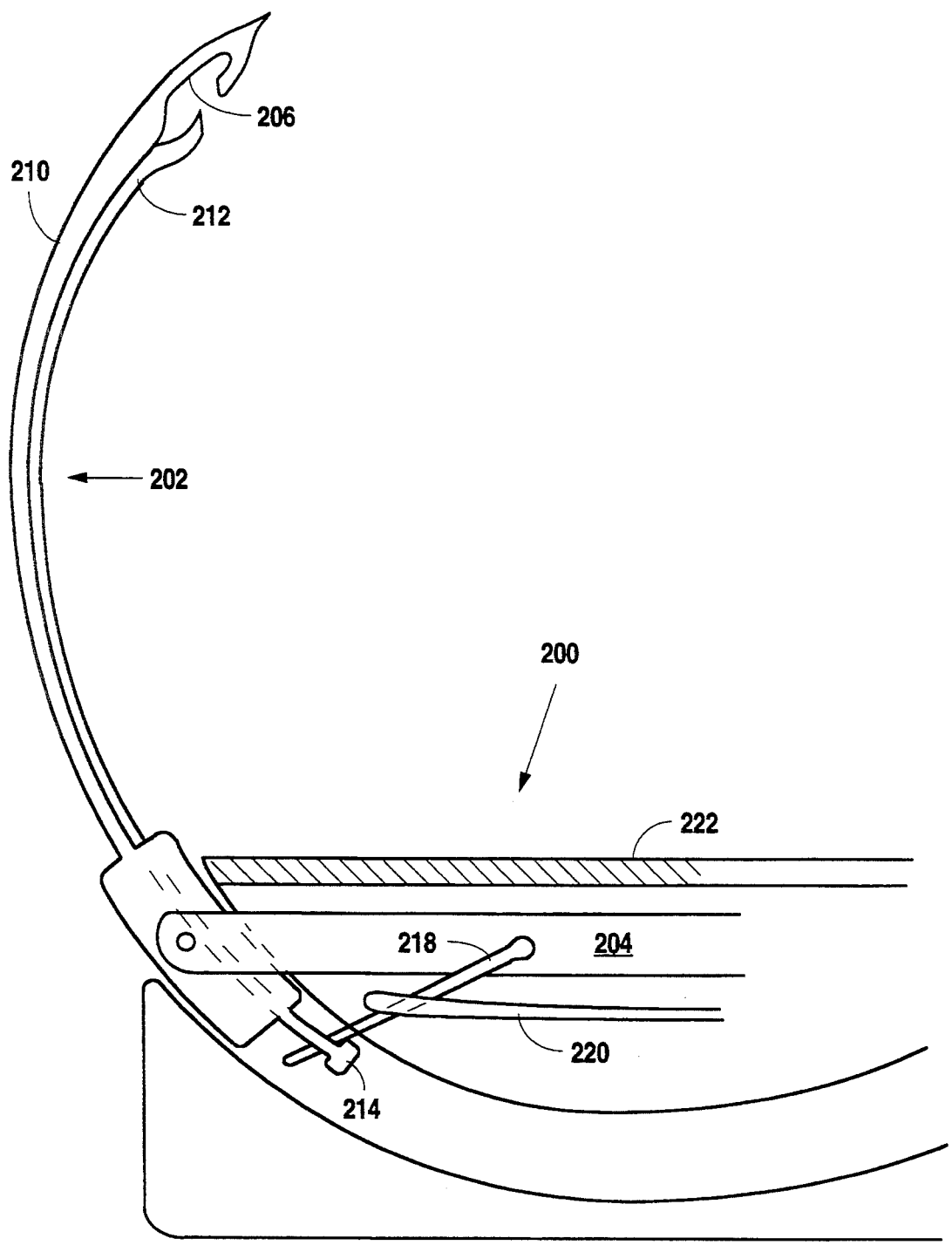
FIG. 17 is an elevational, partially cross sectional view of the lower portion of an second alternate embodiment of Applicant's invention which involves a fixed Reverdin needle with a distally positioned eye (shown open) the needle being in a fully extended position in this view.
Figure 18:
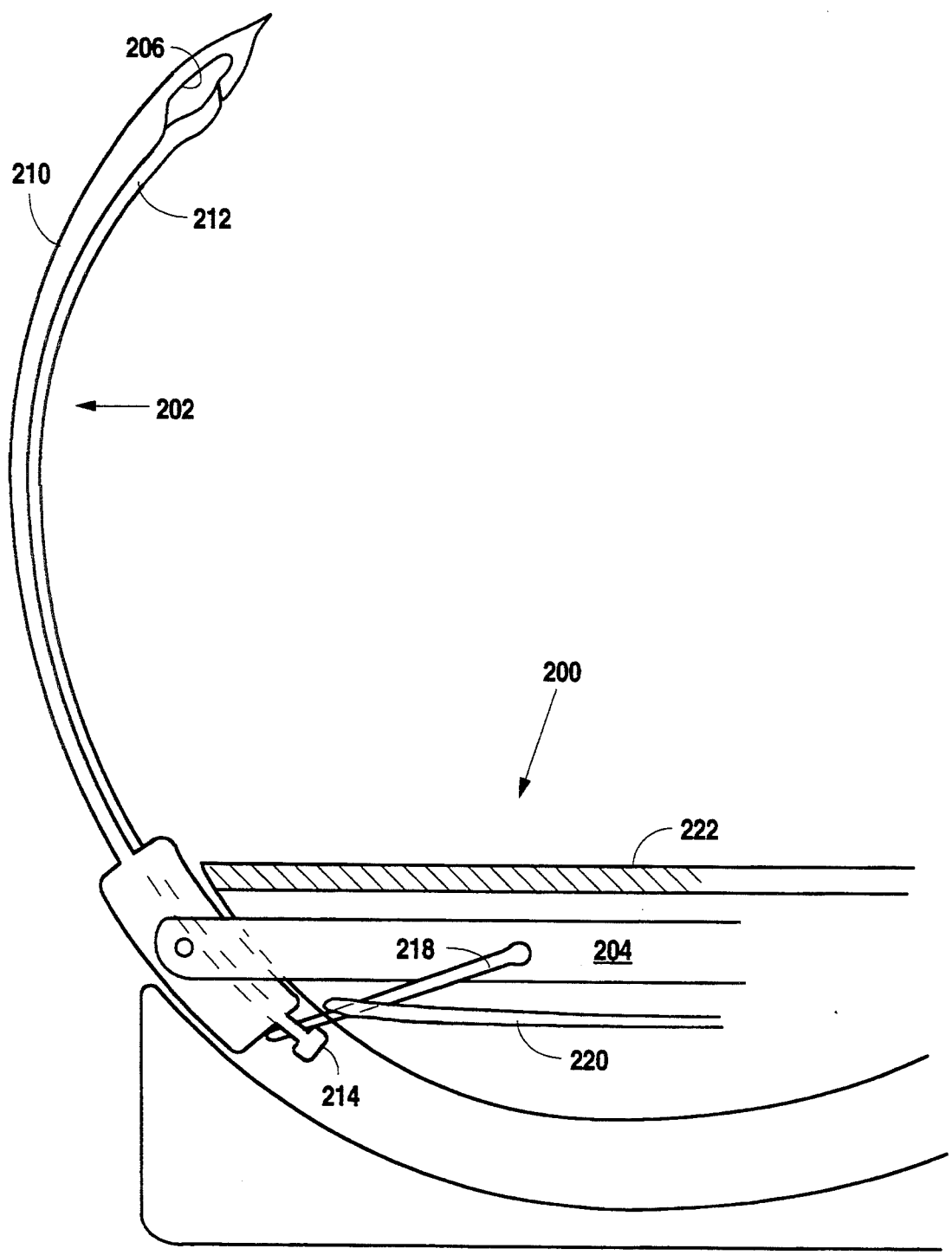
FIG. 18 is an elevational, partially cross sectional view of the lower portion of an second alternate embodiment of Applicant's invention which involves a fixed Reverdin needle with a distally positioned eye (shown closed) the needle being in a fully extended position in this view.

Referring to FIGS. 17 and 18, still another embodiment (instrument 200) of Applicant's invention involves the use a Reverdin needle 202 which is permanently attached to the push rod 204. The needle 202 is advanced and retracted, and operates in the same basic manner as has been shown for instruments 10 and 100.

The Reverdin needle 202 includes two principle components—the fixed tip section 210 and the movable occluding section 212. Tip section 210 is in a hinged relationship with push rod 204. Occluding section 212 is in a channeled relationship with tip section 210 and is spring biased to its closed position (as shown in FIG. 18) by a leaf spring 218 which is attached to the push rod 204. The occluding section 212 extends through the leaf spring 218, the operable relationship therebetween being secured by a flange 214 as depicted. An actuating rod 220 is attached to the leaf spring 218 and extends exterior to the channel member 222 at a portion of the instrument 200 not shown in FIGS. 17 and 18. Retracting the actuating rod 220 flexes the leaf spring 218 so as to draw the occluding section 212 to open the eye 206 of the needle 202.

In use, once the needle 202 is passed through tissue to be sutured, the eye 206 of the needle 202 is opened and a suture thread (not shown) is placed into the eye 206 of the needle 202. The needle 202 is then withdrawn pulling the thread with it back through the tissue.

It is envisioned that the channel member 18 can be formed through the combination of an injection molded plastic insert (not separately shown) and a metal tube which forms an outer casing. The injection molded insert provides the necessary contours for defining the crescent channel 40 and the push rod channel 38. The instrument could be supplied sterile and discarded after use.

The best application for disposable instruments of Applicant's invention would be those with an attached needle with the eye at the tip - either the needle with a fixed eye 102 or a Reverdin needle 202.

Although the invention has been described with reference to specific embodiments, this description is not meant to be construed in a limited sense. Various modifications of the disclosed embodiments, as well as alternative embodiments of the inventions, will become apparent to persons skilled in the art upon the reference to the description of the invention. It is, therefore, contemplated that the appended claims will cover such modifications that fall within the scope of the invention.

I claim:

1. A holder for a surgical needle comprising:

needle holding means for securely grasping a surgical needle, said needle holding means being movably attached to a casing member, said needle holding means comprising a pair of jaws secured and supported for hinge-like relative movement; and guide means for restricting movement of said needle holding means between a first position wherein the surgical needle held by said needle holding means is substantially fully retracted within said casing member, and a second position where substantially all of the surgical needle extends from said casing member, along a curved path defined by said guide means, wherein said guide means is a channel formed within said casing member;

said jaws being sized and shaped for passage through and beyond said channel and whereby said jaws are held in a closed position for securely grasping the surgical needle when said jaws are situated in said channel, but capable of releasing the needle when said jaws exit said channel, said casing member comprises first and second substantially cylindrical channel segments which are rotatably connected one to the other for permitting rotation of said first and second channel segments about a common axis; and actuating means for moving said needle holding means from said first position to said second position, wherein said actuating means is a rod-like member comprising first and second rod segments which are rotatably connected one to the other, said second rod segment being operably connected with said needle holding means and said first rod segment extending outside of said casing member at a terminus of said first channel segment for permitting actuation of said rod-like member by a user of said needle holder 2. A holder for a surgical needle comprising:

needle holding means for securely grasping a surgical needle, said needle holding means being movably attached to a casing member, said needle holding means comprising a pair of jaws secured and supported for hinge-like relative movement; and guide means for restricting movement of said needle holding means between a first position wherein the surgical needle held by said needle holding means is substantially fully retracted within said casing member, and a second position where substantially all of the surgical needle extends from said casing member, along a curved path defined by said guide means, wherein said guide means is a channel formed within said casing member;

said jaws being sized and shaped for passage through and beyond said channel and whereby said jaws are held in a closed position for securely grasping the surgical needle when said jaws are situated in said channel, but capable of releasing the needle when said jaws exit said channel, said casing member comprises first and second substantially cylindrical channel segments which are rotatably connected one to the other for permitting rotation of said first and second channel segments about a common axis; and actuating means for moving said needle holding means from said first position to said second position, wherein said actuating means is a rod-like member comprising first and second rod segments which are rotatably connected one to the other, said second rod segment being operably connected with said needle holding means and said first rod segment extending outside of said casing member at a first terminus of said first channel segment for permitting actuation of said rod-like member by a user of said needle holder, said channel being situated with a second terminus being substantially coincident with a distal end of said casing member and defines a crescent-shaped space for guiding said jaws movement between said first and said second positions in a crescent-shaped path, and wherein said actuating means are operable from outside of said channel means and operate to position said jaws whereby, when the needle is grasped by said jaws and said jaws are in said first position, the needle is fully enveloped within said channel, and upon full actuation of said actuating means, said needle moves from said channel moving in a crescent-shaped path until said jaws exit said second terminus of said channel and said jaws may open to release the needle.

3. A needle holder comprising:

a casing member having a first and a second casing member end and defining an interior space, said casing member having a handle segment and a needle protrusion segment, said handle segment and said needle protrusion segment being rotatably connected to each other whereby said needle protrusion segment may rotate independently of said handle segment, at least a portion of said interior space of said casing member defining a crescent-shaped channel a first crescent channel terminus of which is coincident with said first end of said casing member;

needle grasping means for securely, but reversibly grasping a first terminus of a surgical needle, said needle grasping means being sized and shaped for passage through said crescent-shaped channel;

actuating means for stabilizing said needle grasping means relative to said casing member and for moving said needle grasping means through said crescent-shaped channel between a second position adjacent to a second crescent channel terminus which lies within said interior space of said casing member and a first position close to said first crescent channel terminus whereby actuating said actuating means alternatively moves said needle grasping means in directions toward said first or said second crescent channel termini and accordingly extends or retracts a surgical needle grasped by said needle grasping means relative to said casing member at said first casing member end.

4. A surgical needle holder comprising:

a push rod, said push rod having a push rod user end segment and a push rod needle end segment, each rotatably connected to the other;

a surgical needle pivotally attached to said push rod needle end segment at a first terminus of said push rod, said surgical needle having an apex end and an eye positioned closely adjacent to said apex end;

a casing member, said casing member being a substantially cylindrical body which defines an interior space, a first portion of said interior space taking the form of a crescent-shaped channel and a second portion of said interior space being sized and shaped for accepting a length of said push rod which length includes said needle end push rod segment and, when so accepting said length of said push rod, for properly positioning said surgical needle for passage through said crescent-shaped channel, said crescent-shaped channel being sized and shaped for accepting passage of said surgical needle therethrough and for governing movement of said surgical needle in a crescent-shaped path when said surgical needle moves through said crescent-shaped channel in response to force applied to said surgical needle through said push rod, said casing member having a casing member user end segment and a casing member needle end segment, each said casing member segment being rotatably connected to the other for rotational movement independent of each other.

5. A surgical needle holder comprising:

a push rod, said push rod having a push rod user end segment and a push rod needle end segment, each rotatably connected to the other;

a surgical needle pivotally attached to said push rod needle end segment at a first terminus of said push rod, said surgical needle having first and second needle components, said first needle component being stationarily attached to said push rod and said second needle component being slidably attached to said first needle component, portions of said first and second needle components cooperatively defining an eye positioned closely adjacent to an apex end of said needle, movement of said second needle component in a first direction closing said eye, and movement of said second needle component in a second, opposite direction opening said eye;

a casing member, said casing member being a substantially cylindrical body which defines an interior space, a first portion of said interior space taking the form of a crescent-shaped channel and a second portion of said interior space being sized and shaped for accepting a length of said push rod which length includes said needle end push rod segment and, when so accepting said length of said push rod, for properly positioning said surgical needle for passage through said crescent-shaped channel, said crescent-shaped channel being sized and shaped for accepting passage of said surgical needle therethrough and for governing movement of said surgical needle in a crescent-shaped path when said surgical needle moves through said crescent-shaped channel in response to force applied to said surgical needle through said push rod, said casing member having a casing member user end segment and a casing member needle end segment, each said casing member segment being rotatably connected to the other for rotational movement independent of each other;

needle actuating means attached to said second needle component of said surgical needle for moving said second needle component alternatively in said first and said second directions, said needle actuating means exhibiting at least a portion thereof which is accessible outside of said casing member for actuation by a user of said needle holder.

* * * * *